(12) United States Patent
Bristow

(10) Patent No.: US 9,409,920 B1
(45) Date of Patent: Aug. 9, 2016

(54) METHOD FOR PURIFYING EMAMECTIN BENZOATE AND COMPOSITIONS COMPRISING THE SAME

(71) Applicant: ROTAM AGROCHEM INTERNATIONAL CO., LTD

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/732,993

(22) Filed: Jun. 8, 2015

(51) Int. Cl.
*C07D 493/22* (2006.01)
(52) U.S. Cl.
CPC .................................. *C07D 493/22* (2013.01)
(58) Field of Classification Search
CPC .................................................. C07D 493/22
See application file for complete search history.

(56) References Cited

U.S. PATENT DOCUMENTS

| 5,288,710 | A * | 2/1994 | Cvetovich | C07H 19/01 514/30 |
| 6,486,195 | B1 * | 11/2002 | Cvetovich | A01N 43/90 514/450 |

FOREIGN PATENT DOCUMENTS

EP    736252    9/1996

OTHER PUBLICATIONS

Vogel, (Practical Organic Chemistry, 3rd Ed. (1956), Longman Group London, p. 122-136).*
ZhangHaiJian ("Crystallization process optimization of emamectin benzoate" Thesis—Aug. 2010)—in Japanese.*

* cited by examiner

*Primary Examiner* — Valerie Rodriguez-Garcia
(74) *Attorney, Agent, or Firm* — Dickinson Wright PLLC

(57) ABSTRACT

A purification process of emamectin benzoate and compositions comprising the same. The method for purifying emamectin benzoate comprising steps (a): crystallizing emamectin benzoate in a mixture of polar solvent and non-polar solvent; isolating emamectin benzoate crystals; recovering the solvents by distillation; and recovering a crude emamectin benzoate from the solvents; (b): crystallizing emamectin benzoate crystals from step (a) in a polar aprotic solvent; isolating the crystals; recovering the solvents by distillation; and then collecting a crude emamectin benzoate from the solvents; (c): crystallizing emamectin benzoate crystals collected from step (b) in the mixture of polar solvent and non-polar solvent; isolating the crystals; recovering the solvents by distillation; and collecting a crude emamectin benzoate; wherein the purity of the crystals obtained from step (c) is 99%.

1 Claim, 1 Drawing Sheet

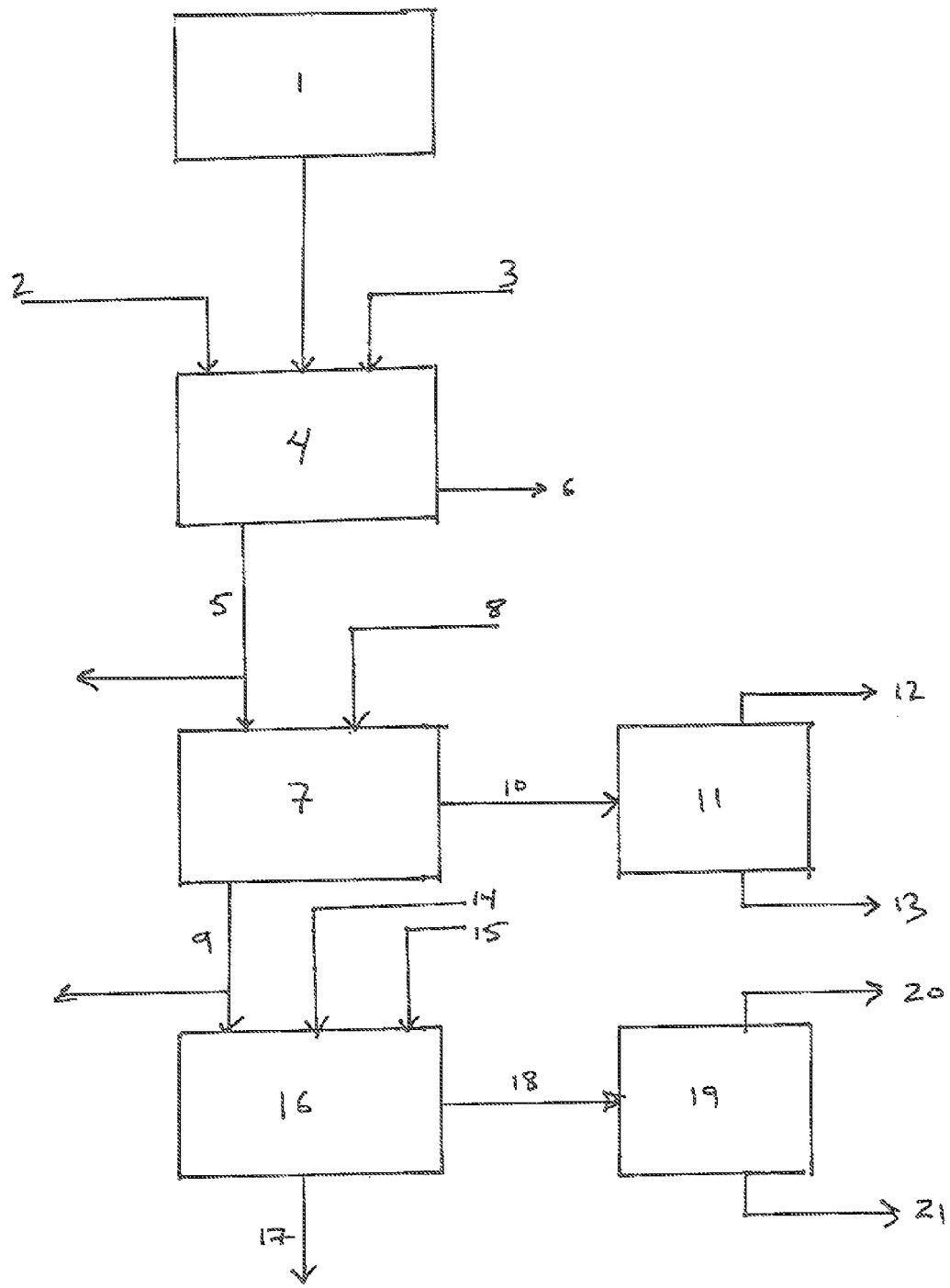

METHOD FOR PURIFYING EMAMECTIN BENZOATE AND COMPOSITIONS COMPRISING THE SAME

BACKGROUND

1. Field

The present disclosure relates to a novel purification process of emamectin benzoate and to compositions comprising emamectin benzoate purified using the same process.

2. Description of Related Art

Emamectin is a potent insecticide which controls many pests such as thrips, leafminers, and worms including alfalfa caterpillar, beet armyworm, cabbage looper, corn earworm, cutworms, diamondback moth, tobacco budworm, tomato fruitworm and tomato pinworm. Emamectin (4"-deoxy-4"-epi-N-methylamino avermectin B1a/B1b) is described in U.S. Pat. No. 4,874,749 and in Cvetovich, R. J. et al, J. Organic Chem. 59:7704-7708, 1994 (as MK-244).

U.S. Pat. No. 5,288,710 describes salts of emamectin that are especially agrochemically valuable. These salts of emamectin are valuable pesticides, especially for combating insects and representatives of the order Acarina. Some pests for which emamectin is useful in combating are listed in European Patent Application EP-A 736,252.

US2003/0068788 discloses a nucleotide sequence which encodes a P450 monooxygenase for making emamectin from avermectin. But, the purity of the resulting product is usually lower than 50%.

Emamectin is famous for its high efficacy and potency in insecticidal effect. However, the purity of emamectin used in commercial formulations nowadays is typically only around 95%. Due to the technical limitations, it is difficult to achieve a satisfactory purity without a dramatic increase in cost. Accordingly, there remains a need for a cost-effective purification method for emamectin benzoate which can be applied in the commercial industry.

SUMMARY

Usually, purity and yield are inversely proportional to each other. To increase purity, one can repeat the purification process. However, the repetition results in a decrease in yield due to losses occurring in each repetition. Conversely, to increase yield, one can reduce the number of repetitions of a purification process, but lower purity is obtained. In the embodiments of this invention, a purification process is presented that produces a high purity product without a significant reduction in yield by wisely recovering solvent and active ingredient during the purification process. Put another way, the purification process according to embodiments of the invention proceeds along parallel pathways. The first, or primary, parallel pathway, involves a sequence of at least three crystallization phases, wherein emamectin benzoate crystals are recrystallized at least three times from a sequence of solvents, with each successive recrystallization providing increasing yields of increasingly pure emamectin benzoate crystals. In a second parallel pathway, a quantity of emamectin benzoate crystals is recovered from the solvent remaining after the second crystallization phase of the primary crystallization pathway. The emamectin benzoate crystals recovered from this second pathway are generally not as pure as those recovered from the primary crystallization pathway. In a third parallel pathway, a quantity of emamectin benzoate crystals is recovered from the solvent remaining after the third crystallization phase of the primary crystallization pathway. These emamectin benzoate crystals are generally not as pure as those recovered from the primary crystallization pathway, but are generally more pure than those recovered from the second parallel pathway.

The improved purification process according to an embodiment of the invention can yield a purity of about 99%. The process is particularly suitable for manufacturing emamectin benzoate on a commercial scale.

The embodiments of the invention provides a method for purifying emamectin benzoate, comprising:
(a) a first recrystallizing phase, comprising:
 (i) dissolving emamectin benzoate in a mixture of at least one polar solvent and at least one non-polar solvent;
 (ii) isolating a first portion of purified emamectin benzoate crystals from the solvent mixture;
 (iii) recovering at least some of the solvents, e.g., by distillation; and
 (iv) recovering the first portion of purified emamectin benzoate crystals;
(b) a second recrystallizing phase, comprising:
 (i) dissolving at least some of the first portion of purified emamectin benzoate crystals from step (a) in at least one polar aprotic solvent;
 (ii) isolating a second portion of purified emamectin benzoate crystals from the polar aprotic solvent;
 (iii) recovering the second portion of purified emamectin benzoate crystals;
 (iv) recovering at least some of the polar aprotic solvent; and
 (v) isolating and collecting a first quantity of entrained emamectin benzoate crystals from the solvent;
(c) a third recrystallizing phase, comprising:
 (i) dissolving at least some of the second portion of purified emamectin benzoate crystals collected from step (b) in a mixture of at least one polar solvent and at least one non-polar solvent;
 (ii) isolating a third portion of purified emamectin benzoate crystals from the mixture of solvents;
 (iii) recovering the third portion of purified emamectin benzoate crystals;
 (iv) recovering at least some of the solvents; and
 (v) isolating and collecting a second quantity of entrained emamectin benzoate crystals from the solvent.

In step (a), the purity of emamectin benzoate can be dramatically increased from about 60% to about 80%, more particularly about 70%, in the starting emamectin benzoate crystals to about 80% to about 95%, more particularly about 90% in the first portion of purified emamectin benzoate. About 60 to 90% by weight, more particularly about 80% by weight, of solvent can be recovered, which may be effected according to any technique known in the art, preferably distillation.

In step (b), the purity of emamectin benzoate can be further increased from about 80% to about 95%, more particularly from about 90% in the first portion of purified emamectin benzoate to about 96% to about 98%, more particularly about 97% in the second portion of purified emamectin benzoate. About 60 to 90% by weight, more particularly about 80% by weight of solvent can be recovered from this step as well, which may be effected according to any technique known in the art, preferably distillation. It was surprising to find that about 7 to about 12% by weight, more particularly, about 9% by weight, of emamectin benzoate (based upon the weight of pure emamectin benzoate in the first portion of purified emamectin benzoate) can be recovered in this step in the first quantity of entrained emamectin benzoate crystals from the solvent. This emamectin benzoate generally has a purity of from about 55% to about 70%, more particularly of about 65%.

In step (c), the purity of emamectin benzoate can be further increased from about 96% to about 98%, more particularly about 97%, in the second portion of purified emamectin benzoate to about 99% in the third portion of purified emamectin benzoate. About 60 to 90% by weight, more particularly about 80% by weight of solvent can be recovered from this step as well, which may be effected according to any technique known in the art, preferably distillation. It was surprising to find that additionally about 5 to about 8% by weight, more particularly about 6.5% by weight, of emamectin benzoate (based upon the weight of pure emamectin benzoate in the second portion of purified emamectin benzoate) can be recovered in this step in the second quantity of entrained emamectin benzoate crystals from the solvent.

From steps (a) to (c), about 60 to 90% by weight, more particularly about 80% of the solvents can be recovered from each step. It was surprising to find that about 12% to about 20% by weight, more particularly about 15.5% by weight, of crude emamectin benzoate in total can be recovered and re-used in the purification process, so that more than about 12% to about 20% by weight, more particularly about 15.5% by weight can be saved from the expense of expensive raw material emamectin benzoate.

The purification process disclosed herein, in addition to providing highly purified emamectin benzoate, does not require conversion into or production of emamectin phosphate or emamectin free base. Moreover, the purification process disclosed herein does not require the introduction of a seed crystal.

BRIEF DESCRIPTION OF DRAWING

Aspects and embodiments of the invention can be more clearly understood by reference to the accompanying drawing, which is intended to illustrate, but not to limit, the scope of the invention and of the appended claims.

FIG. 1 is a flow diagram of an embodiment of the purification process disclosed herein.

DETAILED DESCRIPTION OF SPECIFIC EMBODIMENTS

Various aspects of the invention can be more clearly understood by reference to the following description of specific embodiments, which are intended to illustrate and exemplify, but not to limit, the scope of the invention and of the appended claims.

As used herein, the term "about" when used in connection with a numerical amount means somewhat more or less than the numerical amount to a deviation of 5% of the numerical amount.

The embodiments of the invention can be more clearly understood by reference to the particular embodiment shown schematically as a flow diagram in FIG. 1, which is intended to be illustrative, and not limiting, of the scope of the invention or the appended claims.

In FIG. 1, emamectin benzoate 1 is provided, desirably from a conventional production process. In first recrystallizing phase 4, emamectin benzoate 1 is combined with, and dissolved in, at least one polar solvent 2 and at least one nonpolar solvent 3. These solvents can be supplied separately to the first recrystallizing phase 4, as schematically indicated in FIG. 1, or as a pre-mixed mixture of solvents. A first portion of purified emamectin benzoate 5 is recovered from first recrystallization phase 4, as is at least some of the solvent 6, which can include polar solvent, nonpolar solvent, or a combination thereof.

At least some of the first portion of purified emamectin benzoate 5 is mixed in a second recrystallization phase 7 with at least one polar aprotic solvent 8. A second portion of purified emamectin benzoate 9 is recovered from second recrystallization phase 7, along with at least some polar aprotic solvent 10. At least a portion of recovered polar aprotic solvent 10 is subjected to a solvent separation phase 11, wherein a first quantity of entrained emamectin benzoate 12 is recovered, as is a quantity of polar aprotic solvent 13.

At least some of the second portion of purified emamectin benzoate 9 is mixed with at least one polar solvent 14 and at least one nonpolar solvent 15 in a third recrystallization phase 16. A third purified portion of emamectin benzoate 17 is recovered from third recrystallization phase 16. At least a portion of recovered solvent 18 is subjected to a solvent separation phase 19, wherein a second quantity of entrained emamectin benzoate 20 is recovered, as is a quantity of solvent 21.

In an embodiment of the invention, the polar solvent used in step (a) can be DCM, THF, ethyl acetate, butyl acetate, acetone, DMF, acetonitrile, DMSO, propylene carbonate, formic acid, n-butanol, isopropanol, n-propanol, ethanol, methanol, acetic acid, nitromethane or a combination of any of said solvents, i.e. one or more solvents may be used as the polar solvent, which includes 1, 2, 3, 4, 5 and more solvents in combination. Butyl acetate is more preferred.

In an embodiment of this invention, the non-polar solvent used in step (a) can be pentane, cyclopentane, hexane, cyclohexane, benzene, toluene, 1,4-dioxane, chloroform and diethyl ether or a combination of any of said solvents, i.e. one or more solvents may be used as the non-polar solvent, which includes 1, 2, 3, 4, 5 and more solvents in combination. Hexane is more preferred.

In an embodiment of the invention, polar aprotic solvent used in step (b) can be DCM, THF, ethyl acetate, butyl acetate, acetone, DMF, acetonitrile, DMSO, propylene carbonate or a combination of any of said solvents, i.e. one or more polar aprotic solvents, which includes 1, 2, 3, 4 5 or more solvents in combination.

In an embodiment of the invention, the polar solvent used in step (c) can be DCM, THF, ethyl acetate, butyl acetate, acetone, DMF, acetonitrile, DMSO, propylene carbonate, formic acid, n-butanol, isopropanol, n-propanol, ethanol, methanol, acetic acid, nitromethane or a combination of any of said solvents, i.e. one or more solvents may be used as the polar solvent, which includes 1, 2, 3, 4, 5 and more solvents in combination. Ethyl acetate is more preferred.

In an embodiment of this invention, the non-polar solvent used in step (c) can be pentane, cyclopentane, hexane, cyclohexane, benzene, toluene, 1,4-dioxane, chloroform and diethyl ether or a combination of any of said solvents i.e. one or more solvents may be used as the non-polar solvent, which includes 1, 2, 3, 4, 5 and more solvents in combination. Hexane is more preferred.

In step (a), the weight ratio of the polar to the non-polar solvent is generally from about 3:1 to about 1:1, preferably from about 2:1 to about 1:1, even more preferably from about 1.5:1 to about 1:1, most preferably about 1:1. The preferred combination of solvents is butyl acetate and hexane. The combination of butyl acetate and hexane in a weight ratio of about 2:1 is the most preferred.

In step (c), the weight ratio of the polar to the non-polar solvent is from about 3:1 to about 1:1, preferably from about 2:1.5 even more preferably about 2:1. The preferred combination of solvents is ethyl acetate and hexane. The combination of ethyl acetate and hexane in a weight ratio of 2:1 is the most preferred.

The invention, in an embodiment, also embraces compositions comprising the high purity emamectin benzoate, i.e. having a purity of 97%, preferably 98%, more preferably 99% or even more preferred more than 99%, all based on the emamectin benzoate compound. In an embodiment, the invention also relates to compositions of emamectin benzoate produced by the purification processes described herein, and in particular such emamectin benzoate having the purities described above.

Preference is given to use compositions comprising less than 20% by weight of the compound of emamectin benzoate, particularly preferably less than 15% by weight, particularly preferably less than 10% by weight, especially preferably less than 6% by weight, most preferably is 4% and 5% by weight, of emamectin benzoate for the formulation.

The activity of emamectin benzoate as a pesticidal agent is known in the art and is used in a commercial scale. Emamectin benzoate in high purity produced according to this present disclosure finds use in controlling of pests and pest infestations. Techniques for formulating and using emamectin benzoate are known in the art, for example, as disclosed in the documents discussed hereinbefore. Emamectin benzoate resulting from the processes disclosed herein may be formulated and applied in an analogous manner.

Accordingly, in a further aspect, the invention provides a pesticidal composition comprising emamectin benzoate as described herein.

Accordingly, an embodiment of the invention furthermore provides processes for preparing compositions for controlling pests using the emamectin benzoate in high purity and compositions comprising emamectin benzoate for controlling pests, which compositions were obtained from emamectin benzoate in high purity.

The high purity of emamectin benzoate can be converted in a known manner into the customary formulations, such as suspension concentrates, oil-based suspension concentrates, soluble granules, dispersible concentrates, emulsifiable concentrates (emulsion concentrates), emulsion seed dressings, suspension seed dressings, granules, micro-granules, suspo-emulsions, water-soluble granules, water-soluble concentrates and water-dispersible granules, using suitable auxiliaries and carriers or solvents. Here, the active compound should be present in a concentration from about 0.1% to 20% by weight of the total mixture, i.e., in the amounts sufficient to achieve the required dosage level. The formulations are prepared, for example, by extending the emamectin benzoate in high purity with water, solvents and/or carriers, using, if appropriate, emulsifiers and/or dispersants, and/or other auxiliaries These formulations are prepared in a known manner by mixing the active compounds with customary additives, for example, customary extenders and also solvents or diluents, colorants, wetting agents, dispersants, emulsifiers, antifoams, thickeners and also water.

Suitable extenders include, for example, water, polar and nonpolar organic chemical liquids. The nonpolar organic chemical liquids can be any from the classes of the aromatic and non-aromatic hydrocarbons (such as paraffins, alkylbenzenes, alkylnaphthalenes, chlorobenzenes), the alcohols (such as methanol, ethanol) and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

In some embodiments, the wetting agent may comprise a nonionic surfactant. Such preferred nonionic surfactants include, but are not limited to, alcohol oxyalkylates, alkyl phenol oxyalkylates, nonionic esters such as sorbitan esters and alkoxylates of sorbitan esters. Examples of suitable surfactants include, but are not limited to, castor oil alkoxylates, fatty acid alkoxylates, lauryl alcohol alkoxylates, nonylphenol alkoxylates, octylphenol alkoxylates, tridecyl alcohol alkoxylates, such as POE-10 nonylphenol ethoxylate, POE-100 nonylphenol ethoxylate, POE-12 nonylphenol ethoxylate, POE-12 octylphenol ethoxylate, POE-12 tridecyl alcohol ethoxylate, POE-14 nonylphenol ethoxylate, POE-15 nonylphenol ethoxylate, POE-18 tridecyl alcohol ethoxylate, POE-20 nonylphenol ethoxylate, POE-20 oleyl alcohol ethoxylate, POE-20 stearic acid ethoxylate, POE-3 tridecyl alcohol ethoxylate, POE-30 nonylphenol ethoxylate, POE-30 octylphenol ethoxylate, POE-34 nonylphenol ethoxylate, POE-4 nonylphenol ethoxylate, POE-40 castor oil ethoxylate, POE-40 nonylphenol ethoxylate, POE-40 octylphenol ethoxylate, POE-50 nonylphenol ethoxylate, POE-50 tridecyl alcohol ethoxylate, POE-6 nonylphenol ethoxylate, POE-6 tridecyl alcohol ethoxylate, POE-8 nonylphenol ethoxylate, POE-9 octylphenol ethoxylate, mannide monooleate, sorbitan isostearate, sorbitan laurate, sorbitan monoisostearate, sorbitan monolaurate, sorbitan monooleate, sorbitan monopalmitate, sorbitan monostearate, sorbitan oleate, sorbitan palmitate, sorbitan sesquioleate, sorbitan stearate, sorbitan trioleate, sorbitan tristearate, POE-20 sorbitan monoisostearate ethoxylate, POE-20 sorbitan monolaurate ethoxylate, POE-20 sorbitan monooleate ethoxylate, POE-20 sorbitan monopalmitate ethoxylate, POE-20 sorbitan monostearate ethoxylate, POE-20 sorbitan trioleate ethoxylate, POE-20 sorbitan tristearate ethoxylate, POE-30 sorbitan tetraoleate ethoxylate, POE-40 sorbitan tetraoleate ethoxylate, POE-6 sorbitan hexastearate ethoxylate, POE-6 sorbitan monstearate ethoxylate, POE-6 sorbitan tetraoleate ethoxylate, and/or POE-60 sorbitan tetrastearate ethoxylate. Preferred nonionic surfactants include alcohol oxyalkyalates such as POE-23 lauryl alcohol and alkyl phenol ethoxylates such as POE (20) nonyl phenyl ether. Other applicable nonionic surfactants are esters such as sorbitan monooleate.

Suitable dispersants and/or emulsifiers include those which are appropriate to be used in, e.g. seed dressing formulations and can be any of nonionic, anionic, and cationic dispersants customarily adopted in agrochemical formulations. It is preferred to use nonionic or anionic dispersants or mixtures of nonionic or anionic dispersants. The examples of preferred nonionic dispersants are alkylphenol polyglycol ethers, ethylene oxide-propylene oxide block polymers, and tristyrylphenol polyglycol ethers, as well as any of their sulphated or phosphated derivatives. The examples of preferred anionic dispersants are polyacrylic salts, lignosulphonates, and arylsulphonate-formaldehyde condensates.

Suitable antifoaming agents include those which are appropriate to be used in, e.g., seed dressing formulations and can be any of foam-inhibiting substances customarily adopted in agrochemical formulations. It is preferred to use magnesium stearate and silicone defoamers.

Suitable thickeners include those which are appropriate to be used in, e.g. seed dressing formulations and can be any substances which can be used for such purposes in agrochemical compositions. It is preferred to use cellulose derivatives, acrylic acid derivatives, xanthan, modified clays, and highly disperse silica.

Inorganic pigments, namely Prussian Blue, iron oxide and titanium oxide are possible to be used. In addition, FD&C Blue No. 1 and organic dyestuffs, namely alizarin dyestuffs, azo dyestuffs and metal phthalocyanine dyestuffs, and trace nutrients, namely salts of iron, manganese, boron, copper, cobalt, molybdenum and zinc can also be used.

The active compound according to the invention can be present in its commercially available formulations and in the use forms, prepared from these formulations, as a mixture with other active compounds, such as herbicides, acaricides, insecticides, bactericides, nematicides, fungicides, growth-regulating substances, attractants, safeners, semiochemicals, sterilizing agents or fertilizers.

A mixture with other known active compounds, such as herbicides, fertilizers, growth regulators, safeners, semiochemicals, or else with agents for improving the plant properties, is also possible When the active compound(s) are used as insecticides, according to an embodiment of the invention, they can be present in their commercially available formulations and in the use forms mixed with synergistic agents. The mentioned synergistic agents are those compounds which increase the action of the active compounds but are not necessary for the active.

When the active compound(s) used as insecticides, according to an embodiment of the invention, they can be present in their commercially available formulations and in the use forms as a mixture with inhibitors. The mentioned inhibitors are those able to reduce degradation of the active compound after use in the environment of the plant, on the surface of plant parts or in plant tissues.

All plants and plant parts can be treated with compositions according to an embodiment of the invention. Plants to be understood in the present context shall mean all plants and plant populations such as desired and undesired wild plants or crop plants (including wild crop plants). Crop plants can be plants which can be obtained by conventional breeding and optimization methods or by biotechnological and genetic engineering methods or by combinations of these methods, including the transgenic plants and including the plant cultivars which can or cannot be protected by plant breeders' rights. Plant parts to be understood in the present context shall mean all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment, according to an embodiment of the invention, on the plants and plant parts with the active compounds is carried out directly or by allowing the compounds to act on their surroundings, habitat or storage space in any customary treatment manners, namely, by dipping, spraying, vaporizing, fogging, broadcasting, painting on/in the case of propagation material, particularly on/in the case of seed and applying one or more coats.

Embodiments of the present invention are illustrated by the following specific Examples.

EXAMPLES

Synthesis of Emamectin Benzoate Crude Material

Emamectin benzoate was prepared by the described in U.S. Pat. No. 5,288,710, and the purity was about 70%.

Example 1

Purification of Emamectin Benzoate Crude Material 1.1 Step (a)

420 g (purity=69.1%) of emamectin benzoate crude material and 739 g of butyl acetate were added to a flask. The flask was slowly heated to 52° C. under stirring (20 r/min). It was then slowly cooled from 52° C. to 38° C. in 4 hours and further kept at that temperature for 1 hour. 345 g of hexane was slowly added in 1 hour. The flask was then cooled to 20° C. in 4 hours and kept for 10 hours at that temperature. The content was filtered and dried. 231.6 g emamectin benzoate was obtained. The solvent was recovered, at a rate of about 80% by weight, by distillation, without recovery of additional emamectin benzoate. The purity of the recovered emamectin benzoate crystals was 90% and the yield obtained was 72%.

1.2 Step (b)

Emamectin benzoate crystals obtained from step (a) and 400 ml of acetone was added into 1000 ml of a flask. The flask was heated to 50° C. under stirring (200 r/min). It was then slowly cooled from 50° C. to 20° C. in 6 hours and further kept at that temperature for 10 hours. The content was filtered and dried. 194.1 g of emamectin benzoate crystals was obtained. The purity of the emamectin benzoate crystals was 96.7% and the yield was 89.6%. 28.9 g of emamectin benzoate crystals was recovered from the remaining solvent, and had a purity of 63.56%. The solvent, in an amount of about 80% by weight, was recovered by distillation.

1.3 Step (c)

Emamectin benzoate obtained from step (b) and 320 ml of ethyl acetate was added into a flask. The flask was slowly heated to 50° C. 160 g hexane was slowly added over 1 hour and further kept at that temperature for 0.5 hours. The flask was cooled slowly from 50° C. to 20° C. over 5 hours and kept at that temperature for 10 hours. 175.9 g of emamectin benzoate crystals was obtained. The purity of emamectin benzoate is 99.4%, and the yield was 93.1%. In addition, 14.1 g of emamectin benzoate was recovered from the solvent at a purity of 85.25%. The solvent, in an amount of about 80% by weight, was recovered by distillation.

Example 2

Preparation of Emulsifiable Concentrate (EC) Formulation

The liquid components listed in Table 1 below were, in any order, mixed under stirring at room temperature until a homogeneous liquid was obtained. Solid components were dissolved in the resulting mixture. The emamectin benzoate was obtained from Example 1.

TABLE 1

| Ingredients | Weights % | Function |
| --- | --- | --- |
| Emamectin benzoate 99% | 5.05 | Active compound |
| Butylated hydroxytoluene BHT | 1.00 | Antioxidant |
| Paraffinic oil | 6.40 | Liquid carrier |
| POE 30 castor oil | 9.00 | Liquid carrier |
| Tristyrylphenol 54M ethoxylate (Emulsogen TS54) | 9.00 | Emulsifier |
| VP/VA copolymer (Luvitec VA 64 from BASF) | 18.00 | Dispersant |
| 1-Hexanol | 51.55 | Solvent |

Example 3

Preparation of Suspension Concentrate (SC) Formulation

The liquid components listed in Table 2 below are, in any order, mixed under stirring at room temperature until a homogeneous liquid was obtained. Solid components were dissolved in the resulting mixture. The emamectin benzoate was obtained from Example 1.

TABLE 2

| Ingredients | Weights % | Function |
| --- | --- | --- |
| Emamectin benzoate, 99% | 5.05 | Active compound |
| Tristyrylphenol 54M ethoxylate (Emulsogen TS54) | 9.00 | Emulsifier |
| VP/VA copolymer (Luvitec VA 64 from BASF) | 2.00 | Emulsifier |
| Sodium N-methyl N-oleyl aturate | 9.00 | Surfactant |
| Sodium alkyl naphalene sulonate | 18.00 | Surfactant |
| Alkylpolyvinylpyrrolidone | 2.00 | Thickening agent |
| Butylated hydroxytoluene (BHT) | 1.00 | Antioxidant |
| Water | 53.95 | Filler |

Example 4

Preparation of Soluble Granules (SG) Formulation

The liquid components listed in Table 3 below are, in any order, mixed with stirring at room temperature until a homogeneous liquid was obtained. Solid components were dissolved in the resulting mixture. The emamectin benzoate was obtained from Example 1.

TABLE 3

| Ingredients | Weights % | Function |
| --- | --- | --- |
| Emamectin benzoate, 99% | 5.05 | Active compound |
| 2,6-Di-tert-butyl-4-methylphenol | 3.00 | Antioxidant |
| Sodium dodecyl sulfate | 10.00 | Surfactant |
| Sodium methylenedinaphalene disulphonate | 5.00 | Surfactant |
| Fatty alcohol-polyoxyethylene ether | 4.00 | Surfactant |
| Lactose | 72.95 | Filler |

The invention claimed is:

1. A method for purifying emamectin benzoate comprising:
   (a): crystallizing emamectin benzoate in a mixture of butyl acetate and hexane; isolating emamectin benzoate crystals; recovering the solvents by distillation; and recovering a crude emamectin benzoate from the solvents;
   (b): re-crystallizing emamectin benzoate crystals from step (a) in acetone; isolating the crystals; recovering the solvents by distillation; and then collecting a crude emamectin benzoate from the solvents;
   (c): re-crystallizing emamectin benzoate crystals collected from step (b) in a mixture of ethyl acetate and hexane; isolating the crystals; recovering the solvents by distillation; and collecting a crude emamectin benzoate; wherein the purity of the crystals obtained from step (c) is 99%.

* * * * *